United States Patent [19]

Hopkins

[11] Patent Number: 4,468,455

[45] Date of Patent: Aug. 28, 1984

[54] CELL CULTURE CONTROL

[75] Inventor: Thomas R. Hopkins, Bartlesville, Okla.

[73] Assignee: Phillips Petroleum Company, Bartlesville, Okla.

[21] Appl. No.: 212,169

[22] Filed: Dec. 2, 1980

[51] Int. Cl.³ .................... C12Q 3/00; C12M 1/34
[52] U.S. Cl. ....................... 435/3; 435/291; 435/802; 435/813
[58] Field of Search ............ 435/3, 291, 802, 813

[56] References Cited

U.S. PATENT DOCUMENTS

| | | | |
|---|---|---|---|
| 3,010,881 | 11/1961 | Markhof | 195/117 |
| 3,156,537 | 11/1964 | McLeod | 23/288 |
| 3,384,553 | 5/1968 | Caslansky et al. | 195/95 |
| 3,586,605 | 6/1971 | Hosler | 195/28 |
| 3,645,846 | 2/1972 | Imada et al. | 195/28 R |
| 3,649,842 | 3/1972 | Thornhill et al. | 307/106 |
| 3,672,953 | 6/1972 | Coty et al. | 195/28 |
| 3,926,737 | 12/1975 | Wilson et al. | 195/28 |
| 3,926,738 | 12/1975 | Wilson et al. | 195/28 |
| 3,933,593 | 1/1976 | Sternberg | 195/103.5 R |

OTHER PUBLICATIONS

Douglas M. Considine and S. D. Ross, editors, Handbook of Applied Instrumentation McGraw-Hill, pp. 1–9, 10 and 11; 1964.

Douglas M. Considine, editor; Process Instruments and Controls Handbook McGraw-Hill, 10-92, 93 and 94; 1957.

Takeshi Kobayashi et al., Biotechnology and Bioengineering Symp. No. 9 pp. 73–83; 1979.

Martin Frobisher, Fundamentals of Microbiology, 8th Ed. pp. 52–55; 1970.

Primary Examiner—Robert J. Warden
Attorney, Agent, or Firm—Bernhard H. Geissler

[57] ABSTRACT

In a cell culture process, the addition of an additive is only carried out after it has been determined that the previous addition of additive has caused at least a minimum change in metabolic activity of the cells.

16 Claims, 3 Drawing Figures

CELL CULTURE CONTROL

BACKGROUND OF THE INVENTION

Cell culture processes such as fermentation processes have received considerable attention in recent years. Examples for such processes are aerobic fermentation processes with yeasts or bacteria. One product of such fermentation processes can be single cell protein.

Various control methods have been described in the prior art for controlling cell culture processes. Since cell culture processes involve biological conversions directed toward the maintenance and multiplication of cellular organisms or cells, control operations of such biological processes during cell culture are critical and at time, can be and have been very difficult. It has been described in the art that aerobic cultivation of yeast can be controlled by adding molasses to the culture medium. The concentration of dissolved oxygen in the culture medium is used in this known process to control the addition of molasses. To improve reliability of controlled cell culture processes remains a continuing goal in the art.

THE INVENTION

It is an object of this invention to provide a new cell culture process in which an additive is added to the cell culture medium, responsive to a metabolism activity determination.

It is another object of this invention to provide a cell culture process wherein an additive is added to the medium only after determination that the cell culture is biologically in a condition to be able to utilize the additive effectively.

A further object of this invention is to provide an apparatus for carrying out the process of this invention.

These and other objects, advantages, details, features and embodiments of this invention will become apparent to those skilled in the art from the following description of the invention, the appended claims and the drawing in which FIG. 1 is a schematic representation of the control system of this invention when applied to a fermentation operation.

Figure 1:
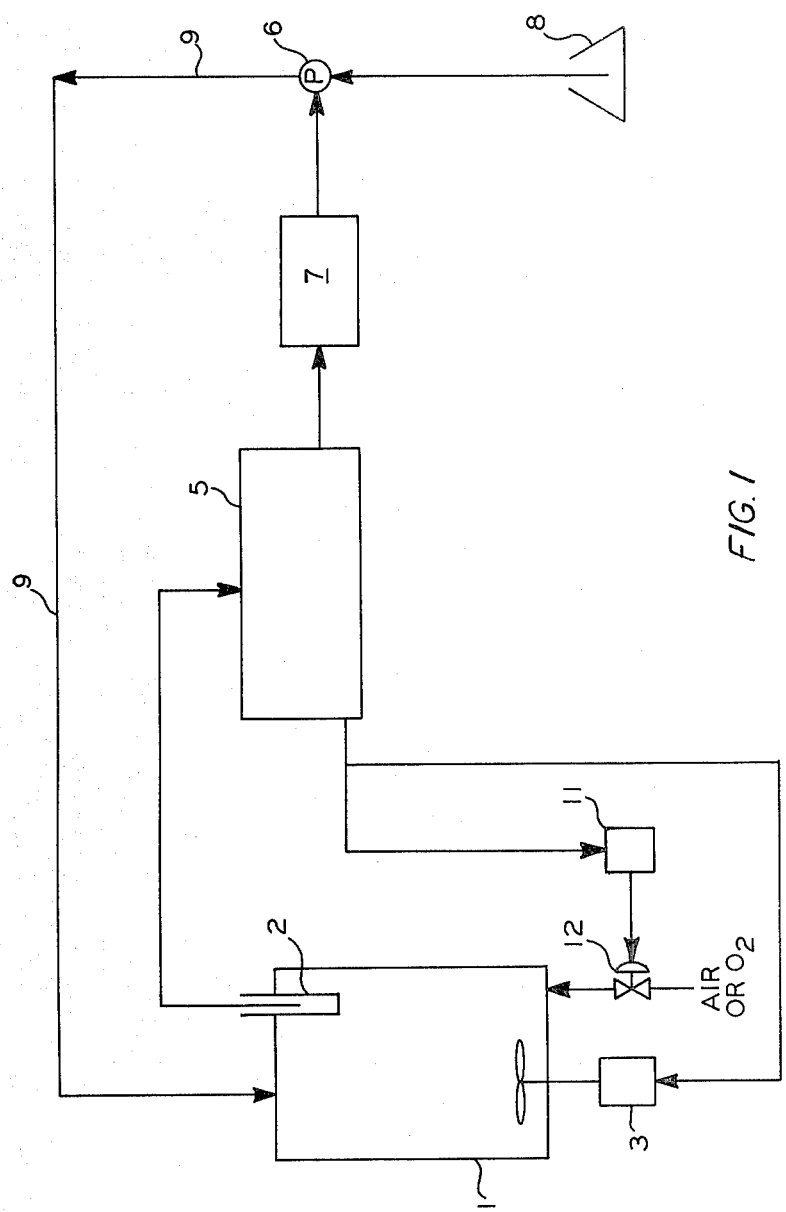

In accordance with this invention, a cell culture process is provided in which an additive is added to the cell culture medium in a given amount, but only if the previous addition has caused at least a minimum change of metabolic activity in the cell culture. In other words, in accordance with this invention and, except for the very first addition of additive during the start-up operation, the given quantity of additive is added to the cell culture medium only after it has been determined that the cell culture medium reacted to the previous addition in the way it was expected to. Generally, the cell culture is expected to increase its metabolic activity following an addition of an amount of additive.

In the presently preferred control mode, the addition of a fixed amount of additive is carried out only after two events have been established. The first event is that at least a minimum change of metabolic activity in the cell culture has been caused by the previous addition of the additive. The second event is that the metabolic activity has again reached an activity set-point. Generally, therefore, the metabolic activity of the cell culture will reach a minimum value (low metabolic activity set-point). Then a given amount of additive is added to the cell culture medium. Thereupon, the metabolic activity of the cells will increase and the absolute value of the metabolic activity will rise above the low set-point or minimum value. Thereby, the required minimum change in metabolic activity has been established. After a certain period of time, the cell culture will again lose metabolic activity due to the consumption of some of the additive. The metabolic activity will again reach the set-point or minimum value and the addition of a fixed quantity of additive is repeated. Should, for some reason, the cell culture not react to the addition of the additive in the expected way, then no further additive is added even though the absolute value of the metabolic activity of the cell culture may be such that the additive would otherwise be added.

A second embodiment of this invention relates to an apparatus for growing a cell culture in a medium in a controlled manner. This apparatus comprises a housing wherein the cell culture in the medium can be subjected to growth conditions. A sensor is operatively connected to the medium in the housing. This sensor can determine the metabolic activity of the cell culture. A controller is operatively connected with the sensor. This controller is capable of generating a manipulating signal if, following a previous manipulating signal, the sensor transmitted at least a minimum change of metabolic activity in the cell culture. Means for adding a given quantity of additive to the medium in the housing, responsive to the manipulating signal, are operatively connected to the controller.

In the following, the invention will be described in connection with further preferred features and embodiments.

In accordance with one variation of the process of this invention, the control of addition of an ingredient to an aerobic fermentation system, which ingredient is toxic for the microorganism above a certain concentration, is controlled responsive to the dissolved oxygen in the fermentation medium. A fixed quantity of the ingredient is added to the fermentation zone when the concentration of dissolved oxygen reaches an upper set-point, but only if the previous addition of said ingredient has caused at least a minimum decrease in the concentration of the dissolved oxygen. In this embodiment of the invention, it is, of course, assumed that the change of dissolved oxygen considered has been caused by the addition of the ingredient alone and not by a change of, e.g. aeration or oxygen addition from the outside.

In the aerobic fermentation process which is emcompassed by this invention, a microorganism in contact with a liquid culture medium and free oxygen containing gas is subjected to fermentation conditions and the concentration of dissolved oxygen in the liquid culture medium is determined. Responsive to this determination of the dissolved oxygen, the flow of an additive into the culture medium is controlled. The improvement, in accordance with this invention, resides in the fact that a controller, by means of a manipulating signal, will cause the addition of additive only if the previous addition of the additive has caused the dissolved oxygen content in the medium to be decreased by at last a minimum value. Only then will the controller generate the manipulating signal, responsive to the fact that the dissolved oxygen has increased again to a set-point value.

Various additives are incorporated into the liquid culture medium of a fermentation process depending upon what the desired production is. Examples of additives which when reaching a certain concentration are toxic to the microorganism are given in the following.

The additive may be the carbon source, i.e., the main product consumed by the microorganism. Thus, it is well known that methanol, which is consumed by certain microorganisms, is also highly toxic to those same microorganisms when present in too high a concentration in the liquid culture medium for the bacteria or the yeast. Another example of additives which are toxic after reaching a certain concentration is the addition of a vitamin analogue to a fermentation process. Such vitamin analogues are frequently added to fermentation processes together with glucose which is not toxic. If too much of the mixture of vitamin analogue and glucose are added to the fermentation zone, the microorganism also may be killed. In another example, one could be delivering a water insoluble substrate dissolved in a non-aqueous solvent, such as a steroid in acetone. While too much steroid might not harm the microorganism, an excess of acetone could poison the organism.

The determination of the change of metabolic activity of the microorganism, prior to allowing the controller to add another fixed quantity of additive to the fermentation system, is an important feature of this invention. To illustrate this feature in connection with a single cell protein fermentation, the following is provided assuming the fermentation system has a simple controller attached to a dissolved oxygen sensor such that a sudden increase in dissolved oxygen above a set limit signals the complete consumption of methanol in the fermenter and triggers the release of a fixed quantity of methanol to such a fermentation system. Consider also that a pH controller fails. This failure would cause the organism to reduce considerably the rate of metabolism. Thus, if the controller adding pulses of fixed quantity of methanol to such a fermentation system would be allowed to operate regardless of the metabolic activity behavior of the microorganism, the control system would eventually add so much methanol to the system to completely kill the culture. The reason for this resides in the fact that the organism would be metabolizing so much slower after the pH upset that the oxygen content would remain high and the controller therefore would continually add further "slugs" of methanol thereby inhibiting even further the organisms' activity. Opposite to this operation the present invention provides for a process where the controller, following one addition of a fixed quantity of an additive such a methanol, is not allowed to add a further quantity of an additive before the metabolic activity of the microorganism has changed at least a minimum value. We will call this a feed-on-demand system.

While changes in the state of cell metabolism can be monitored using a dissolved oxygen probe, it is also within the scope of this invention to use the same feed-on-demand controller linked to transducers which e.g. monitor changes in culture pH (J. D. Brooks and J. L. Meets, *J. Gen. Microbiol.*, Vol. 77, p. 513 (1973))

exhaust gas $CO_2$ (D. Zabriskie, W. Armiger and A. E. Humphrey, *Abstr.* 168th Ann. Meet. Amer. Chem. Soc. Micro. 38 (1974))

redox potential in the cultivation broth (S. Y. Huang and C. F. Wu, J. Ferment. *Technol.* Vol. 52, p. 818 (1974), and L. Kjaergaard and B. B. Joergensen, *Biotechnol. Bioengn. Symp.* No. 9, p. 85 (1979))

fluorescence intensity of the culture (D. W. Zabriskie, W. B. Armiger and A. E. Humphrey, *Abstr. Annu. Meet. Amer. Soc. Microbiol.* 75, 195 (1975), and D. W. Zabriskie and A. E. Humphrey, *Appl. Environ. Microbiol.* Vol. 35, p. 337 (1978))

or substrate or product concentrations using enzyme electrodes (J. W. Hewetson, T. H. Jong and P. P. Grey, *Biotechnol. Bioengn. Symp.* No. 9, p. 125 (1979))

or rate of heat production. The latter measurement is particularly uncomplicated and reliable. In well-stirred reactors having efficient cooling equipment, significant changes in heat flux can be measured in periods of less than one minute after the substrate is depleted in the culture broth.

In accordance with a presently preferred variation of the first embodiment, the flow of oxygen-containing gas into the liquid culture medium in an aerobic fermentation is also controlled. It is presently preferred to have this control achieved responsive to a lower-limit set-point for the concentration of the dissolved oxygen determined in the process. Thus, in this variation, a first control signal is generated when the concentration of dissolved oxygen exceeds an upper set-point and this first control signal causes the addition of additive as described, i.e., only if the previous addition has caused the dissolved oxygen content to drop below a given value. When the dissolved oxygen concentration reaches a lower set-point, the flow of free oxygen-containing gas into the system is increased. Thereby, the oxygen content of the liquid culture medium is maintained above a minimum level. This lower set-point has nothing to do with the determination of the minimum of dissolved oxygen following an additive addition.

In accordance with a further variation of the first embodiment of this invention, a specific operation for start-up of a cell culture process and system as described is provided. In this start-up operation, the fixed quantity of material added responsive to the control signal is small. This quantity is then continuously or discontinuously increased until a desired level for steady state operation is reached. The "slug size" may thus vary during the start-up procedure from one unit to 100 units or be within smaller ranges. The reason for this increase in the quantity added during each feed step is that the quantity of cells in the culture system during the start-up is small but increasing. Therefore, in the example of an aerobic fermentation, the time required for observing a reduction in the concentration of dissolved oxygen, caused by the total consumption of the material added to the liquid culture medium, is shorter the smaller the quantity added is. For start-up operations, it is, however, desirable that this period, i.e., the pulse-period or period of additive addition, be long. Therefore, the "fixed" quantities of the material added to the cell culture system will preferably increase roughly at the same rate as the number of cells in the system increases until a steady state operation is reached. The quantity of material or additive added to the cell culture medium can be varied during the start-up period as described in a variety of ways. A feed pump can be varied in speed and/or the time for turning on the feed pump to achieve the addition of the "fixed" amount additive can be changed from a longer to a shorter period of vice versa. Typical pulse times for the addition of the "fixed" quantity of material will be between ten seconds and thirty minutes; preferably between fifteen seconds and fifteen minutes. The control process of this invention can be used both in a batch type cell culture operation and in a continuous cell culture operation. The presently preferred operation relates to a continuous cell culture process. In this continuous process, a mixture of additive and nutrient is fed in distinct charges to the cell culture system with nothing fed to the system between such charges. Instead of pulses of a mixture of nutrient and the additive, it is also possible to feed the nutrient and the additive separately as pulses to the system. Furthermore, it is within the scope of this invention to feed the nutrient continuously to the system and to add only the additive in pulses either separately to the fermentation system or into the nutrient stream. The additive as described above is one which, at or above certain concentration, is toxic for the microorganism.

The following is more detailed description of the invention with specific reference to the control of a fermentation process involving cultures which consume a carbon source, wherein this carbon source has concentration-dependent toxic or inhibitory properties. Such a situation is, for instance, present when microorganisms are grown on methanol, ethanol, or their corresponding aldehydes.

Growth of some cultures can be difficult if the carbon source being used has concentration-dependent toxic or inhibitory properties. Such is the case when microorganisms are grown on methanol, ethanol, or their corresponding aldehydes. Under these circumstances, it is important to feed the substrate to the growing culture at precisely the same rate at which it is being metabolized. If excessive substrate concentrations build up, growth of the culture will be impaired. Conversely, if addition of the carbon source lags behind, the culture will not grow at its maximum rate and the time required to start up an innoculated fermenter to its continuous growth phase will be delayed. In practice, this means that starting up a culture to a steady condition with carbon substrates such as methanol requires constant monitoring of a large number of variables of the fermenter. This procedure is often tedious and lacks reliability. Furthermore, automation of the control procedure frequently involves a complicated and costly computer system.

If a culture is grown under conditions where the dissolved oxygen is not in excess, changes in the dissolved oxygen concentration in the fermenter can be used to monitor the matabolic status of the growing culture. Under suitable growing conditions, oxygen tension measurements will be linked to the rate of microbial utilization of the carbon substrate. Utilizing this relationship between dissolved oxygen concentration in the fermenter and carbon substrate utilization, a simple apparatus has been designed and tested which, when incorporated into a continuous fermentation system, will automatically start up an inoculated culture without further manual adjustment. The apparatus is a feed-on-demand controller. The apparatus simplifies the growing of microorganism on carbon substrates which, at moderate concentrations, are inhibitory or toxic to the growing microorganism. The following specific operation is described with reference to the drawings.

EXAMPLE

Reference is made to FIG. 1. Continuous fermentation was carried out in a 4 liter Microferm fermentor (New Brunswick Scientific Co.) equipped with an In-gold combination pH probe. The broth was maintained at a constant pH with a controller. Concentrated ammonium hydroxide solution was used for pH adjustment. Temperature was kept constant by circulating cold or hot water through a stainless steel coil placed inside the fermentor vessel 1 and by integral turbine mixing means 3. Dissolved oxygen was monitored by means of a commercially available galvanic-type probe 2. A recorder controller 5 is connected to the galvanic-type probe 2. In the recorder controller 5, the signal from the galvanic-type probe 2 is converted into a control signal and the oxygen content is recorded. The control system itself will be described in more detail in connection with FIG. 2. The recorder 5 generates a control signal which, through a time delay relay 7, causes a pump 6, for a duration of time defined by the time delay relay 7, to pump a methanol feed medium from a reservoir 8 via conduit 9 into the fermenter 1.

Figure 2:
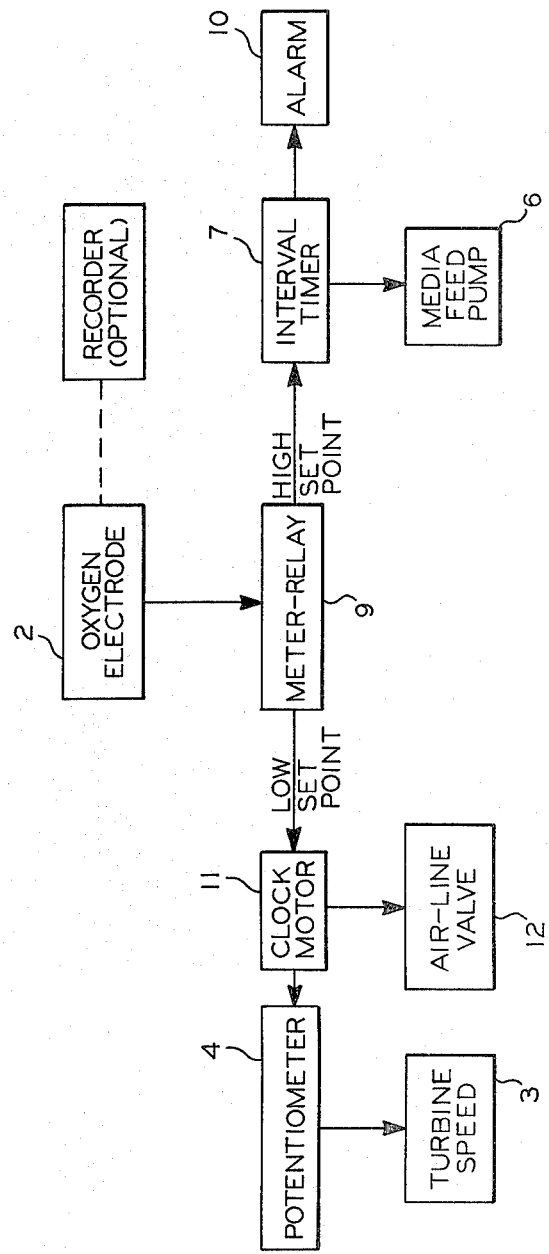
FIG. 2 is a block diagram of the feed-on-demand controller of this invention.

The general configuration of the feed-on-demand controller is shown in FIG. 2. The meter relay 9 (Beede Electrical Instrument Co., type MR 23-05), interval timer 7 (Industrial Timer Corp., model PAF-15M), alarm 10 (Mallory Sonalert Alarm, type SC 110) and miscellaneous switches, indicator lights, sockets and binding posts were placed in a small aluminum cabinet. External to the cabinet is the clock motor 11 and feed pump 6 (FMI lab pump, Models RPG-150 and RPG-54). The microampere signal coming from the dissolved oxygen probe 2 is converted to a millivolt signal with an operational amplifier integrated circuit.

Culture of Microorganisms

The yeast, *Hansenula polymorpha* (NRRL Y-11,170), was maintained on YM agar slants (Difco) and a high temperature bacterial culture (NRRL B-8158) isolated from soil was stored in lyophilized form. Cultures were initially started in shake flasks using a simple mineral salts medium similar to that described by Levine and Cooney, D. W. Levine and C. L. Cooney, Appl. Microbiol., 26. 982 (1973) and 0.5 percent methanol. Continuous culture was initiated by adding one liter of the shake flask culture to 1.5 liters of fresh medium. Typically a suitable medium, FM-12, would include the following:

| One Liter Aqueous Solution | |
|---|---|
| Component | Amount |
| $H_3PO_4$ (85%) | 2.0 mL |
| KCl | 1.0 g |
| $MgSO_4.7H_2O$ | 1.5 g |
| $CaCl_2.2H_2O$ | 0.2 g |
| NaCl | 0.1 g |
| Trace mineral solution | 5.0 mL |

The trace mineral solution is formulated according to the following recipe:

| One Liter Aqueous Solution | |
|---|---|
| Component | Amount |
| $CuSO_4.5H_2O$ | 0.06 g |
| KI | 0.08 g |
| $FeCl_3.6H_2O$ | 4.80 g |
| $MaSO_4H_2O$ | 0.30 g |
| $Na_2MoO_4.2H_2O$ | 0.20 g |
| $ZnSO_4.7H_2O$ | 2.00 g |
| $H_3BO_3$ | 0.02 g |

The yeast culture was maintained at 40° C. and pH 3.5 and the mixed bacteria culture at 55° C. and pH 6.3. Feed methanol concentration was 12.5 percent. Steady state cell densities in excess of 50 g (dry weight) per liter were achieved.

Another example for a composition of suitable medium 41-11 is

| One Liter Aqueous Solution | |
| --- | --- |
| Component | Amount |
| $H_3PO_4$ (85%) | 3.25 mL |
| KCl | 2.5 g |
| $MgSO_4.7H_2O$ | 2.25 g |
| $CaCl_2.2H_2O$ | 0.3 g |
| $H_2SO_4$ (Conc) | 0.5 mL |
| Trace Mineral Solution (10 ×) | 3.0 mL |
| $MnSO_4$ Solution (10 ×) | 2.5 mL |
| MeOH (for example 12.5%) | 125 mL |
| ($MnSO_4$ Sol (10 ×) = 3 g $MnSO_4$ 1/liter of deionized water) | |

| Trace Mineral Solution | |
| --- | --- |
| Component | Amount (g/L) |
| $CuSO_4.5H_2O$ | 0.6 |
| KI | 0.8 |
| $MnSO_4.H_2O$ | 3.0 |
| $Na_2MoO_4.2H_2O$ | 2.0 |
| $H_3BO_3$ | 0.2 |
| $ZnSO_4.7H_2O$ | 20.0 |
| $FeCl_3.6H_2O$ | 48.0 |
| Add 3 mL/L of conc $H_2SO_4$ to take out precipitate. | |

CONTROL OPERATION

The feed-on-demand controller monitors the dissolved oxygen tension in the fermenter. The signal from the dissolved oxygen probe is calibrated such that full scale deflection on the meter-relay is equivalent to 100 percent saturation with air. The high set-point from the meter-relay (FIG. 2) is connected through an interval timer which, in turn, activates the methanol feed pump. When the dissolved oxygen concentration exceeds the high set-point of the meter-relay, a single pulse of methanol is delivered for a period of 15 seconds to 15 minutes, depending upon the setting of the interval timer. The added pulse of methanol, the size of which is designed not to reach the inhibitory level, initiates active oxidative metabolism in the microorganism. Oxygen is consumed, the dissolved oxygen tension in the fermenter decreased and remains below the high set-point on the meter-relay 9 until all methanol is used up. When the concentration of methanol approaches a zero level, the metabolic demand for oxygen in the microorganism decreases and the dissolved oxygen tension in the aerated fermenter 1 (FIG. 1) increases. The high set-point on the meter-relay 9 is exceeded and the feed cycle repeats.

If a malfunction occurs during fermentation such as a loss of pH control or the methanol feed pump becomes plugged, the dissolved oxygen tension will not decrease after the pulse of methanol is delivered to the fermenter. Circuitry in the feed-on-demand controller then may trip an alarm 10 about 10 seconds from the termination of a pulse to indicate an abnormal operating condition. No further pulses of methanol are delivered until the abnormal condition is remedied. This logic feature, an important improvement over discontinuous methanol addition using a simple timer, will prevent build up of toxic methanol concentrations in the fermenter. Usually the fermenter malfunction thus can be corrected in time to save the culture.

The meter relay 9 will be reset only when the oxygen electrode signal indicates that the concentration of dissolved oxygen in the culture medium has fallen below a given value which, in the instant operation, is the same value as that which triggers the meter relay to turn on the interval timer and through the interval timer the media pump. Therefore, after the content of the dissolved oxygen has decreased below the given value, the meter relay 9 is reset. The fact that the concentration of dissolved oxygen decreased below this value after the addition of methanol means that the organism is viable, and metabolically active, i.e., consumes both oxygen and methanol. This feature is of importance for this invention since this feature prevents the methanol buildup during situations in which the concentration of dissolved oxygen remains high and thus simulates to the controller a condition as if further methanol would be needed whereas in fact other reasons such as an insufficiently active microorganism or too high an acidity inhibiting the metabolic activity of the microorganism has caused the concentration of dissolved oxygen to stay high after the addition of the methanol.

The feed-on-demand controller can also be used to keep the dissolved oxygen tension in the fermenter 1 above a given level. This features, which can be operated with or without methanol feed control is useful during the time of inoculation and the steady-state phase of continuous fermentation when the cells are growing at an exponentially increasing rate. The low set-point on the meter-relay 9 activates a clock motor linked to either the air line needle valve 12 or the stirring motor 3 speed control (not shown in the drawing) or both. Thus, aeration of the fermentation is automatically paced with the increasing oxygen demand of the growing culture.

Figure 3:
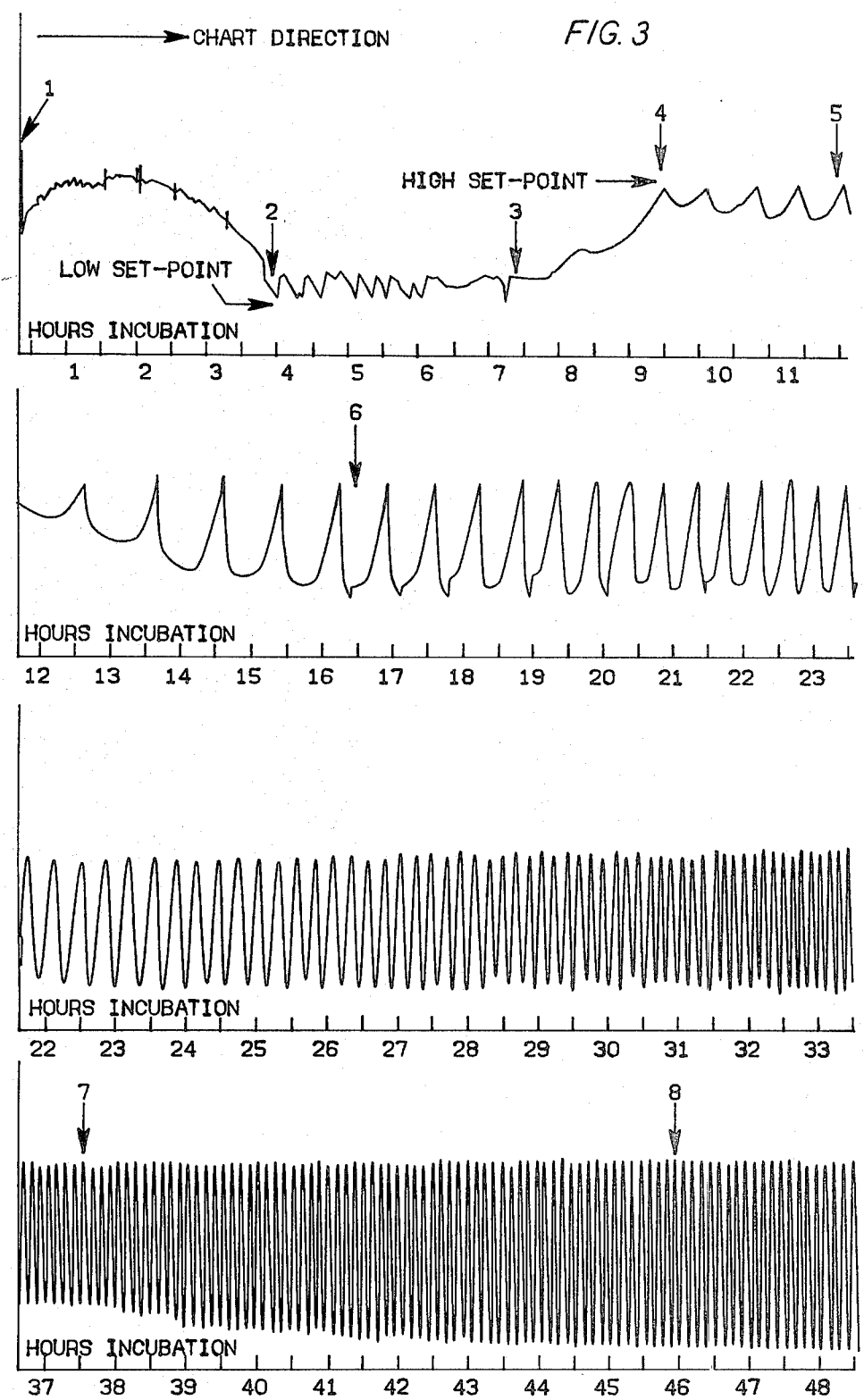
FIG. 3 is a recorder printout showing the oxygen content in a fermentation fluid from start-up to steady-state operation of an aerobic fermentation.

FIG. 3 shows a two-day recording of dissolved oxygen tension in the fermenter 1 from the time of inoculation (point 1) to steady-state conditions under feed-on-demand control. For the first seven hours residual alcohol originally present in the inoculation media was consumed (point 1-3). At approximately 3.5 hours into the fermentation record, the cell density reached a point where automatic step-wise increases of aeration began (point 2). Eventually, the residual methanol in the fermenter was depleted (point 3) and the dissolved oxygen tension began to increase. When the high set-point on the meter-relay 9 was reached (point 4), automatic pulses of methanol began. Initially, the fermenter received 2 mL pulses of 12.5 percent methanol in water. Then 2.5 hours later (point 5) the pulse size was increased to 8 mL pulses of 12.5 percent alcohol. This increase during start-up operation could also be achieved automatically rather than manually. As the culture continued to grow, both the aeration continued to be increased (point 6 and pulses thereafter) and the interval between pulses grew shorter and shorter. Eventually, aeration of the fermenter reached a practical limit (stirrer rate was maximum, further increases in air flow were without effect) and the dissolved oxygen tension dipped close to zero percent oxygen after each pulse of methanol (point 7 to 8). Steady-state growth conditions had been reached. The above results were obtained using a mixed bacterial culture. Similar results were obtained over a longer time scale using yeast. After several trials using different pulse intervals and methanol feed pump settings, it was found that best results were obtained when the methanol pulse interval was about one-third as long as the dissolved oxygen cycle, peak to peak. Pulse intervals as short as 10 seconds (with corresponding increases in pump rate) have been used when the cell density was high and aeration rates were high. At the beginning of a run, a pulse interval of about 10 minutes or more is recommended.

The feed-on-demand controller is designed to automatically control the rate of feed of methanol carbon source and the rate of aeration to cultures being brought up to continuous culture conditions. While the controller could also be used to maintain steady-state growth conditions, the organism is forced to grow in a mode where substrate concentrations oscillate from levels in excess of what can be immediately utilized to near zero concentrations. Under these conditions, the yield coefficient (g cells/100 g methanol) suffers. The yields of both *Hansenula polymorpha* and the mixed bacteria culture were 60 percent of that found in a continuous feed regime. Similar impaired yields were reported in the literature (J. D. Brooks and J. L. Meers, J. Gen. Microbiol., 77, 513 (1973)) where the effect of pulse-feeding substrate on the growth of a methanol utilizing Pseudomonas was examined. The explanation of these decreased yields appear to be that immediately required for their metabolic demands and rapidly oxidize the excess with production of heat only, (I. Goldberg, Porcess Biochem., 12, 12 (1977)). Cultures killed with excessive levels of methanol always had high levels of formaldehyde in the broth. In contrast thereto formaldehyde present in a rapidly growing culture during an operation in accordance with this invention was immeasurably low (<50 ng/mL).

The feed-on-demand controller also proved efficient in handling malfunctions of the fermenter support system. Some system perturbations which would have led to loss of a culture under continuous media feed through buildup of toxic levels of methanol were averted with the feed-on-demand controller. The controller prevents more than one pulse of methanol being delivered to a fermenter when the metabolic status of the organism is changed by mishaps as, for example, deviations in fermenter pH or a drop in fermenter temperature. In most mishaps, the alarm in the controller summoned an operator in time to correct the fault. In certain cases, when the mishap occurred late at night, it was still possible to save the culture the next morning because the culture was not poisoned with excess methanol.

In accordance with a second embodiment of this invention, a fermentation control system is provided for. This control system comprises a sensor capable of generating an oxygen signal responsive to the concentration of the oxygen dissolved in a fermentation medium. This oxygen signal may be a pneumatic signal, an optical and an electrical signal. A controller is operatively connected to this sensor for receiving the oxygen signal. This controller generates a first control signal when both the oxygen signal represents a high set-point for the oxygen concentration and the controller is in its reset condition. Operatively connected to the controller and for receiving the first controller signal, a metering device is provided which causes the feeding of a predetermined quantity of an additive to a fermenter. The controller is equipped with reset means which switch the controller from the reset condition to a deactivated condition after a first control signal is generated. The reset means switch the controller back to its reset or activated conditions whenever the oxygen signal represents a reset-value of oxygen concentration. Frequently, it is possible to use the same value of oxygen concentration for the reset-value and for the high set-point. However, if equipment is used involving a signficant amount of signal noise, it is recommended that a controller be used which has a reset-value for the oxygen concentration that is below the high set-point value for the oxygen concentration. In this instance, the difference between the high set-point and the reset-value for the dissolved oxygen concentration will be significantly larger than the difference in oxygen concentration which corresponds to the signal noise.

In a preferred variation of this control system, the controller is further capable of generating a second control signal whenever the oxygen signal represents a low set-point oxygen concentration. In this variation, the controller is connected to a manipulator which manipulates the air flow into a fermenter. The manipulator is arranged for receiving the second control signal and is designed to increase the air flow by a given amount whenever it receives such a second control signal.

Reasonable variations and modifications which will become apparent to those skilled in the art can be made in this invention without departing from the spirit and scope thereof.

I claim:
1. A cell culture process comprising
   (a) contacting cells with liquid culture medium under growth conditions to allow said cells to metabolize and grow,
   (b) adding a given amount of an additive to said medium which additive is toxic for the culture above a certain concentration, and determining the change of metabolic activity of said cells occurring after said adding,
   (c) repeating step b a plurality of times but each time only if at least a minimum change of metabolic activity was determined in the previous step b.
2. A process in accordance with claim 1 wherein a later addition of an amount of additive is carried out only after a change signal, representative of at least a minimum change of metabolic activity caused by the previous addition, and an activity signal, representative of said metabolic activity having reached an activity set-point, have been generated.
3. A process in accordance with claim 2 wherein said activity signal is generated when the metabolic activity of said cells drops below a set-point.
4. A process in accordance with one of the claims 1 to 3 wherein said cells are microorganisms.
5. A process in accordance with one of the claims 1 to 4 wherein said minimum change of metabolic activity is a minimum increase in the metabolic activity.
6. A process in accordance with claim 1 wherein changes of said metabolic activity are determined by measuring changes in one or more of the following properties:
   (a) culture pH,
   (b) $CO_2$ content of exhaust gas,
   (c) redox potential of the cultivation broth,
   (d) fluorescence intensity of the culture,
   (e) substrate of product concentrations,
   (f) rate of heat production,
   (g) dissolved oxygen concentration.
7. A process in accordance with one of claims 1 to 3 and 6 wherein said cell culture process is an aerobic fermentation, wherein the concentration of dissolved oxygen of said culture medium is determined,
wherein said minimum change of metabolic activity is determined by measuring a minimum decrease in dissolved oxygen following the addition of the additive.

8. A process in accordance with one of the claims 1 to 3 and 6 wherein said additive is the carbon source for a cell culture process.

9. A process in accordance with claim 1 wherein a controller generates a manipulating signal initiating step b responsive to both of the following two signals having been generated:
   (a) a change signal representative of said minimum change in metabolic activity caused by the preceding adding, and
   (b) an activity signal representative of said metabolic activity having reached an activity set-point.

10. A process in accordance with claim 9 wherein metabolic activity is determined by measuring the dissolved oxygen concentration in an aerobic culture medium, high dissolved oxygen concentration being representative when after said adding, the interaction between the additive and the culture causes the dissolved oxygen concentration to decrease.

11. An apparatus for growing a cell culture in a medium comprising
   (a) a housing wherein said cell culture in said medium can be subjected to growth conditions,
   (b) a sensor operatively connected to said medium in said housing,
   (c) said sensor being capable of determining the metabolic activity of said cell culture,
   (d) operatively connected to said sensor a controller generating a manipulating signal if, following the previous manipulating signal, the sensor transmitted at least a minimum change of metabolic activity,
   (e) operatively connected to said controller and for receiving said manipulating signal, means for adding a given quantity of additive to said medium in said housing responsive to said manipulating signal.

12. An apparatus in accordance with claim 11 wherein said controller is designed to generate said manipulating signal only if said sensor transmitted said at least minimum change and if thereafter the absolute value of said metabolic activity has reached a low set-point.

13. An apparatus in accordance with claim 11 wherein said minimum change of metabolic activity is a minimum increase in metabolic activity.

14. An apparatus in accordance with claim 11 wherein said sensor is a sensor for determining the dissolved oxygen concentration in a cell culture medium.

15. An apparatus in accordance with one of the claims 11 to 14 further comprising
   (a) means for continuously passing a stream of free oxygen-containing gas into said housing,
   (b) a control signal generator operatively connected to said means for adding oxygen, which control signal manipulates the flow rate of the free oxygen-containing gas, said control signal being generated by said controller, responsive to a comparison of a dissolved oxygen signal and a dissolved oxygen control signal, the dissolved oxygen signal being representative of the oxygen dissolved in the aerobic cell culture medium in said housing.

16. An apparatus in accordance with claim 11 wherein said sensor is a heat flux sensor and wherein a signal representative of the change of the rate of heat production is converted into said manipulating signal.

* * * * *